(12) United States Patent
Kump et al.

(10) Patent No.: US 7,381,964 B1
(45) Date of Patent: Jun. 3, 2008

(54) METHOD AND SYSTEM OF X-RAY DATA CALIBRATION

(75) Inventors: Kenneth S. Kump, Waukesha, WI (US); James Z. Liu, Glenview, IL (US)

(73) Assignee: General Electric Company, Schenectady, NY (US)

(*) Notice: Subject to any disclaimer, the term of this patent is extended or adjusted under 35 U.S.C. 154(b) by 19 days.

(21) Appl. No.: 10/905,935

(22) Filed: Jan. 27, 2005

Related U.S. Application Data (60) Provisional application No. 60/522,958, filed on Nov. 24, 2004.

(51) Int. Cl.
*G01T 1/20* (2006.01)
(52) U.S. Cl. .............. 250/370.11; 250/370.09
(58) Field of Classification Search ........... 250/370.11, 250/370.09
See application file for complete search history.

(56) References Cited

U.S. PATENT DOCUMENTS

| | | | |
|---|---|---|---|
| 5,103,092 A | 4/1992 | Takahashi et al. | |
| 5,262,871 A | 11/1993 | Wilder et al. | |
| 5,281,803 A | 1/1994 | Ishizuka | |
| 5,508,740 A | 4/1996 | Miyaguchi et al. | |
| 5,514,873 A | 5/1996 | Schulze-Ganzlin et al. | |
| 5,519,227 A * | 5/1996 | Karellas ................. 250/483.1 | |
| 5,608,774 A | 3/1997 | Polichar et al. | |
| 5,661,309 A | 8/1997 | Jeromin et al. | |
| 5,693,948 A | 12/1997 | Sayed et al. | |
| 5,715,292 A | 2/1998 | Sayag et al. | |
| 5,773,832 A | 6/1998 | Sayed et al. | |
| 5,811,790 A | 9/1998 | Endo et al. | |
| 5,828,726 A | 10/1998 | Polichar et al. | |
| 5,867,553 A * | 2/1999 | Gordon et al. ................. 378/4 |
| 5,903,052 A | 5/1999 | Chen et al. | |
| 5,909,478 A | 6/1999 | Polichar et al. | |
| 5,962,856 A | 10/1999 | Zhao et al. | |
| 5,965,872 A | 10/1999 | Endo et al. | |
| 6,049,074 A | 4/2000 | Endo et al. | |
| 6,127,714 A | 10/2000 | Mochizuki | |
| 6,208,708 B1 | 3/2001 | Hoheisel et al. | |
| 6,232,607 B1 | 5/2001 | Huang | |
| 6,239,439 B1 | 5/2001 | Itabashi et al. | |
| 6,255,638 B1 | 7/2001 | Eräluoto et al. | |
| 6,323,891 B1 | 11/2001 | Kitani et al. | |
| 6,331,705 B1 | 12/2001 | Eisen et al. | |

(Continued)

FOREIGN PATENT DOCUMENTS

JP          11271454          10/1999

(Continued)

*Primary Examiner*—David P. Porta
*Assistant Examiner*—Shun Lee
(74) *Attorney, Agent, or Firm*—Ziolkowski Patent Solutions Group, SC (57) ABSTRACT

A process of data calibration and correction is disclosed that utilizes feedback from a temperature sensor of an x-ray detector to isolate or otherwise select an appropriate calibration or correction map that is specific to the temperature of the x-ray detector during data acquisition. The method is also designed to take into account changes in power transients of an x-ray detector between the acquisition of imaging data and the acquisition of offset data. The method is particularly applicable in optimally selecting and applying gain correction, conversion factor, bad pixel, and offset calibrations.

9 Claims, 10 Drawing Sheets

U.S. PATENT DOCUMENTS

| | | |
|---|---|---|
| 6,333,963 B1 | 12/2001 | Kaifu et al. |
| 6,344,652 B1 | 2/2002 | Shoji |
| 6,398,409 B1 | 6/2002 | Brooks |
| 6,453,008 B1* | 9/2002 | Sakaguchi et al. ......... 378/98.7 |
| 6,459,132 B1 | 10/2002 | Mochizuki |
| 6,469,312 B2 | 10/2002 | Agano |
| 6,475,824 B1 | 11/2002 | Kim |
| 6,552,319 B2 | 4/2003 | Pyyhtiä et al. |
| 6,667,480 B2 | 12/2003 | Kajiwara |
| 6,700,126 B2 | 3/2004 | Watanabe |
| 6,707,880 B2 | 3/2004 | Yamayoshi |
| 6,714,623 B2 | 3/2004 | Sako et al. |
| 6,723,592 B2 | 4/2004 | Shih |
| 2002/0005490 A1 | 1/2002 | Watanabe |
| 2002/0005904 A1* | 1/2002 | Mendis ...................... 348/246 |
| 2002/0150214 A1 | 10/2002 | Spahn |
| 2002/0163996 A1* | 11/2002 | Kerrien et al. .............. 378/207 |
| 2002/0181659 A1 | 12/2002 | Watanabe et al. |
| 2002/0195567 A1* | 12/2002 | Ducourant ............. 250/370.11 |
| 2003/0031296 A1 | 2/2003 | Hoheisel |
| 2003/0185342 A1* | 10/2003 | Petrick et al. ............. 378/98.8 |

FOREIGN PATENT DOCUMENTS

| | | |
|---|---|---|
| JP | 2001099942 | 4/2001 |
| JP | 2001198116 | 7/2001 |
| JP | 2001224579 | 8/2001 |
| JP | 2002006049 | 1/2002 |
| JP | 2002014170 | 1/2002 |
| JP | 2002048873 | 2/2002 |
| JP | 2002125960 | 5/2002 |
| JP | 2002131437 | 5/2002 |
| JP | 2003000586 | 1/2003 |
| JP | 2003010175 | 1/2003 |
| JP | 2003014862 | 1/2003 |
| JP | 2003060181 | 2/2003 |
| JP | 2003334184 | 11/2003 |

* cited by examiner

METHOD AND SYSTEM OF X-RAY DATA CALIBRATION

CROSS-REFERENCE TO RELATED APPLICATION

The present invention claims the benefit of U.S. provisional application Ser. No. 60/522,958, filed Nov. 24, 2004.

BACKGROUND OF THE INVENTION

The present invention relates generally to diagnostic imaging and, more particularly, to a method and system of calibrating an x-ray detector to reduce artifacts in an image reconstructed from x-ray attenuation imaging data acquired by the x-ray detector.

X-ray imaging is a non-invasive technique to capture images of medical patients for clinical diagnosis as well as inspect the contents of sealed containers, such as luggage, packages, and other parcels. Increasingly, x-ray systems are being used to non-invasively search and/or screen airplane, boat, and train passengers as well as entrants to court buildings, government offices, sporting events, concerts, and other venues of heightened security interest. To capture these images, an x-ray source irradiates a scan subject with a fan beam of x-rays. The x-rays are then attenuated as they pass through the scan subject. The degree of attenuation varies across the scan subject as a result of variances in the internal composition of the subject. The attenuated energy impinges upon an x-ray detector designed to convert the attenuating energy to a form usable in image reconstruction. A control system reads out electrical charge stored in the x-ray detector and generates a corresponding image. For a conventional, screen film detector, the image is developed on a film and displayed using a backlight.

Increasingly, flat panel, digital x-ray detectors are being used to acquire data for image reconstruction. Flat panel detectors are generally constructed as having a scintillator, which is used to convert x-rays to visible light that can be detected by a photosensitive layer. The photosensitive layer includes an array of photosensitive or detection elements that each store electrical charge in proportion to the light that is individually detected. Generally, each detection element has a light sensitive region and a region comprised of electronics to control the storage and output of electrical charge. The light sensitive region is typically composed of a photoconductor, and electrons are released in the photoconductor when exposed to visible light. During this exposure, charge is collected in each detector element and is stored in a capacitor situated in the electronics region. After exposure, the charge in each detector element is read out using logic controlled electronics.

Each detector element is conventionally controlled using a transistor-based switch. In this regard, the source of the transistor is connected to the capacitor, the drain of the transistor is connected to a readout line, and the gate of the transistor is connected to a scan control interface disposed on the electronics in the detector. When negative voltage is applied to the gate, the switch is driven to an OFF state, i.e. no conduction between the source and drain. On the other hand, when a positive voltage is applied to the gate, the switch is turned ON resulting in connection of the source to the drain. Each detector element of the detector array is constructed with a respective transistor and is controlled in a manner consistent with that described below.

Specifically, during exposure to x-rays, negative voltage is applied to all gate lines resulting in all the transistor switches being driven to or placed in an OFF state. As a result, any charge accumulated during exposure is stored in each detector element capacitor. During read out, positive voltage is sequentially applied to each gate line, one gate at a time. In this regard, only one detector element is read out at a time. A multiplexer may also be used to support read out of the detector elements in a raster fashion. An advantage of sequentially reading out each detector element individually is that the charge from one detector element does not pass through any other detector elements. The output of each detector element is then input to a digitizer that digitizes the acquired signals for subsequent image reconstruction on a per pixel basis. Each pixel of the reconstructed image corresponds to a single detector element of the detector array.

As described above, indirect detection, digital x-ray detectors utilize a layer of scintillating material, such as Cesium iodide (CsI), to convert incident radiation to visible light that is detected by light sensitive regions of individual detector elements of a detector array. Generally, the transistor controlled detector elements are supported on a thin substrate of glass. The substrate, which supports the detector elements as well as the scintillator layer, is supported by a panel support. The panel support is not only designed to support the detector components, but also isolates the electronics that control the detector from the image detecting components. The electronics are supported by the panel support and enclosed by the back cover.

Conventional flat panel detectors have utilized a chiller to regulate the temperature of the detector to be within a given temperature range. The chiller, however, adds to the size, weight, and complexity of the detector. As consumer demand for lighter and more maneuverable x-ray detectors has increased, it has become necessary to design x-ray detectors that do not use a chiller to actively control detector temperature. Specifically, increasingly, flat panel detectors are cooled using natural convection. Since natural convection is a passive means of regulating temperature, it can be difficult to timely maintain detector temperature during heavy detector usage periods. That is, as the number of data acquisitions increases within a given time period, so does the thermal load placed on the x-ray detector. If the intervals between data acquisitions are short, the x-ray detector may not sufficiently cool between data acquisitions to maintain a desired thermal equilibrium. As such, the x-ray detector may be placed into use despite the x-ray detector having a non-ideal temperature or a temperature outside a desired temperature range.

As a result of the acquisition of data when the detector is outside the desired temperature range, image quality is affected. That is, during the image reconstruction process, a number of detector calibrations or data corrections are typically applied to improve image quality. These calibrations and corrections usually assume a given temperature for the x-ray detector during data acquisition. Specifically, the calibration and corrective process typically assumes that the x-ray detector has a temperature within a desired temperature range during the acquisition of imaging data. As such, the calibration and corrective processes do not take into account whether the x-ray detector temperature during data acquisition was outside the presumed temperature range. Moreover, the calibration and corrective measures generally ignore the specific temperature of x-ray detector even when the temperature is within the desired range. By failing to take into account the specific temperature of the x-ray detector or that the temperature is outside a predefined temperature range, the calibration and corrective measures may inadequately or improperly applied.

Also affecting the accuracy and precision of x-ray data calibration that is particularly applicable for offset correction is the time interval between the acquisition of x-ray imaging data and the acquisition of offset imaging data. Offset correction is a calibration process whereby an offset image is acquired without x-rays and used to mask acquired imaging data. The theory behind the offset correction technique is that artifacts attributable to the x-ray detector or scan environment itself may be masked from the imaging data acquired with x-rays. In application, the acquired offset data is used to reconstruct an offset image that is subtracted from the imaging data image. This results in a subtraction of the artifacts in the imaging data image that are also present in the offset image and, thus, improves image quality. As a result of the time differences between the acquisition of imaging data and offset data, power transients may introduce artifacts that are not removed in the subtraction process.

It would therefore be desirable to have a process of calibrating acquired x-ray attenuation data that takes into account the specific temperature of the x-ray detector during data acquisition. It would also be desirable to have a calibration technique that reduces the effect of power transients in an offset image used for offset calibration of imaging data.

BRIEF DESCRIPTION OF THE INVENTION

The present invention is directed to a process of calibrating an x-ray detector that overcomes the aforementioned drawbacks.

A method of data calibration and correction is disclosed that utilizes feedback from one or more temperature sensors, e.g. thermistors, in the cover of an x-ray detector to isolate or otherwise select an appropriate calibration or correction map that is specific to the temperature of the x-ray detector during data acquisition. The method is also designed to take into account changes in power transients of an x-ray detector between the acquisition of imaging data and the acquisition of offset data. The method is particularly applicable in optimally selecting and applying gain correction, conversion factor, bad pixel, and offset calibrations.

Therefore, in accordance with one aspect, the present invention includes an x-ray imaging system having an x-ray detector configured to detect radiation attenuation through a subject to be imaged and output imaging data in response thereto and at least one thermal sensor configured to sense a temperature of the x-ray detector and provide temperature feedback of the x-ray detector. The system further has a processor operationally connected to receive the temperature feedback from the at least one thermal sensor and apply a correction to the output of the x-ray detector specific to the temperature of the x-ray detector.

In accordance with another aspect of the invention, an x-ray detector is disclosed that includes a scintillator configured to emit light in response to reception of radiation and a detector element array configured to output radiographic data and having a plurality of detector elements. Each detector element is configured to detect light from the scintillator and provide an electrical signal that may be processed for image reconstruction. The x-ray detector also has a temperature sensor to provide feedback as to temperature of the x-ray detector and a processor programmed to calibrate the radiographic data output by the detector element array specific to the temperature of the detector element array during radiographic data acquisition.

According to another aspect, the invention is directed to a method of x-ray detector calibration. The method includes determining a temperature of an x-ray detector during data acquisition from a subject to be imaged and selecting a data correction map specific to the temperature of the x-ray detector from a number of stored data correction maps. The selected data correction map is then applied to data acquired by the x-ray detector to reduce artifacts in an image reconstructed from the data acquired by the x-ray detector.

In accordance with yet a further aspect, the present invention includes a method of x-ray data correction that includes the steps of acquiring radiographic data from a subject to be imaged and determining a temperature of an x-ray detector used to acquire the radiographic data. The method also includes the steps of comparing the temperature of the x-ray detector to a temperature-dependent calibration map and identifying those detector elements of the x-ray detector that are presumed corrupted at the temperature of the x-ray detector during data acquisition. The method then ignores data acquired by those detector elements presumed corrupted during image reconstruction.

According to a further aspect of the invention, a method of x-ray data correction is defined by the steps of acquiring radiographic data from a subject to be imaged and determining a temperature of an x-ray detector used to acquire the radiographic data. The method also includes comparing the temperature of the x-ray detector to a database of temperature-dependent gain maps and selecting a temperature-dependent gain map from the comparison. The selected temperature-dependent gain map is then applied to the radiographic data acquired to reduce artifacts in a reconstructed image of the subject.

In accordance with another aspect, the present invention is directed to a method of x-ray data correction. The method includes the steps of acquiring radiographic data from a subject to be imaged and determining a temperature of an x-ray detector used to acquire the radiographic data. The method further includes the steps of comparing the temperature of the x-ray detector to a temperature-dependent x-ray detector sensitivity curve and identifying a conversion factor from the comparison, as well as applying the identified temperature-dependent conversion factor to the radiographic data acquired to achieve a desired brightness in a reconstructed image of the subject.

In accordance with a further aspect, a method of calibrating an offset image for x-ray data correction is provided. The method includes determining a time interval between acquisition of radiographic image data and acquisition of offset image data and determining a magnitude of a power mode transient between the acquisition of radiographic image data and the acquisition of offset image data from the time interval. The method also includes selecting an offset data correction map from a number of offset data correction maps from the magnitude. The selected offset data correction map is designed to reduce a difference between artifacts in the offset image data and the radiographic image data attributable to the power transient.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention will be described with respect to a flat panel, solid-state, indirect detection, and portable digital x-ray detector for use with a mobile x-ray imaging system. However, the present invention is equivalently applicable with other types of x-ray detectors including direct detection digital detectors. Additionally, the present invention may be used with stationary or fixed room x-ray imaging systems. Further, the present application makes reference to an imaging "subject" as well as an imaging "object". These terms are interchangeable and are not intended to limit the scope of the appending claims.

Figure 1:
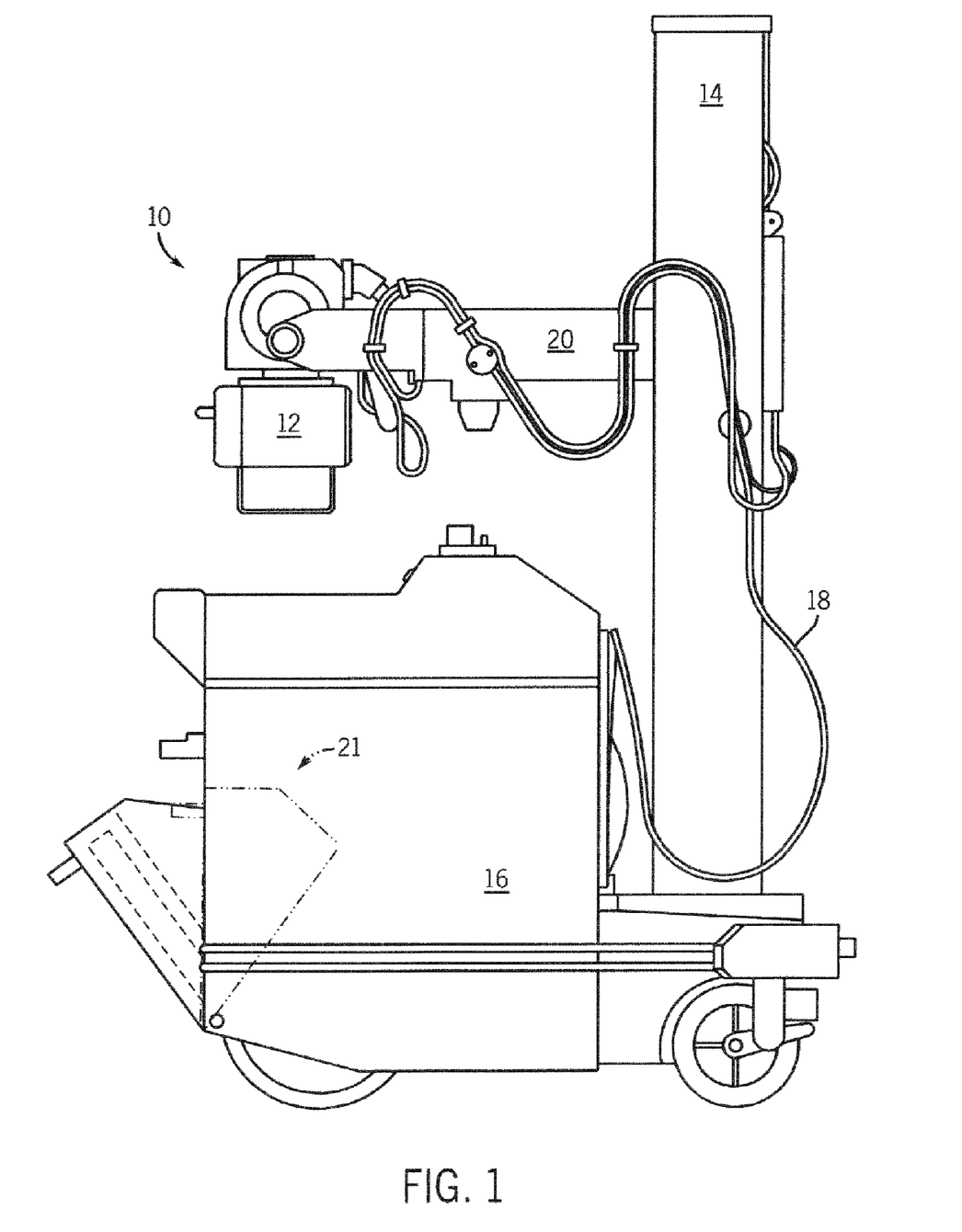
FIG. 1 is a pictorial view of an exemplary mobile x-ray imaging system.

Referring now to FIG. 1, an exemplary mobile x-ray imaging system 10 applicable with a portable x-ray detector incorporating the present invention is shown. An x-ray source 12 is mounted or otherwise secured to an end of horizontal arm 20. Arm 20 allows the x-ray source 12 to be variably positioned above a subject in such a manner so as to optimize irradiation of a particular area of interest. The x-ray source 12 is typically mounted through a gimbal type arrangement (not shown) in column 14. In this regard, the x-ray source may be rotated vertically from a rest or park position on the mobile x-ray unit base 16 to the appropriate position above the subject in order to take an x-ray exposure of the subject. The rotational movement of column 14 is typically limited to a value of 360 degrees or less to prevent entanglement of high voltage cables 18 used to provide electrical power to the x-ray source 12. Cables 18 may be connected to a utility line source (not shown) or a battery (not shown) in the base 16 to energize the x-ray source 12 as well as other electronic components of the system 10.

One skilled in the art will appreciate that system 10 may be equipped or connectable to a display unit (not shown) for the display of images captured from the imaging subject. The mobile system may include a retractable storage bin 21 for storage of an x-ray detector within base 16. The storage bay may also be constructed to regulate the temperature of the stored x-ray detector using passive as well as active thermal control techniques. While only a single stored x-ray detector is shown, it is contemplated that the storage bin may be sized to hold multiple x-ray detectors. Additionally, it is preferred that the storage bin snuggly receive each x-ray detector to limit movement, vibration, stresses, and the like on the stored x-ray detector when the x-ray scanner is being transported. In this regard, the storage bin may include foam or other deformable material to receive an x-ray detector in a tightly fashion as well dampen any force that may otherwise be placed on a stored detector when the x-ray scanner is jarred. The storage bin may receive x-ray detectors of various sizes.

Figure 2:
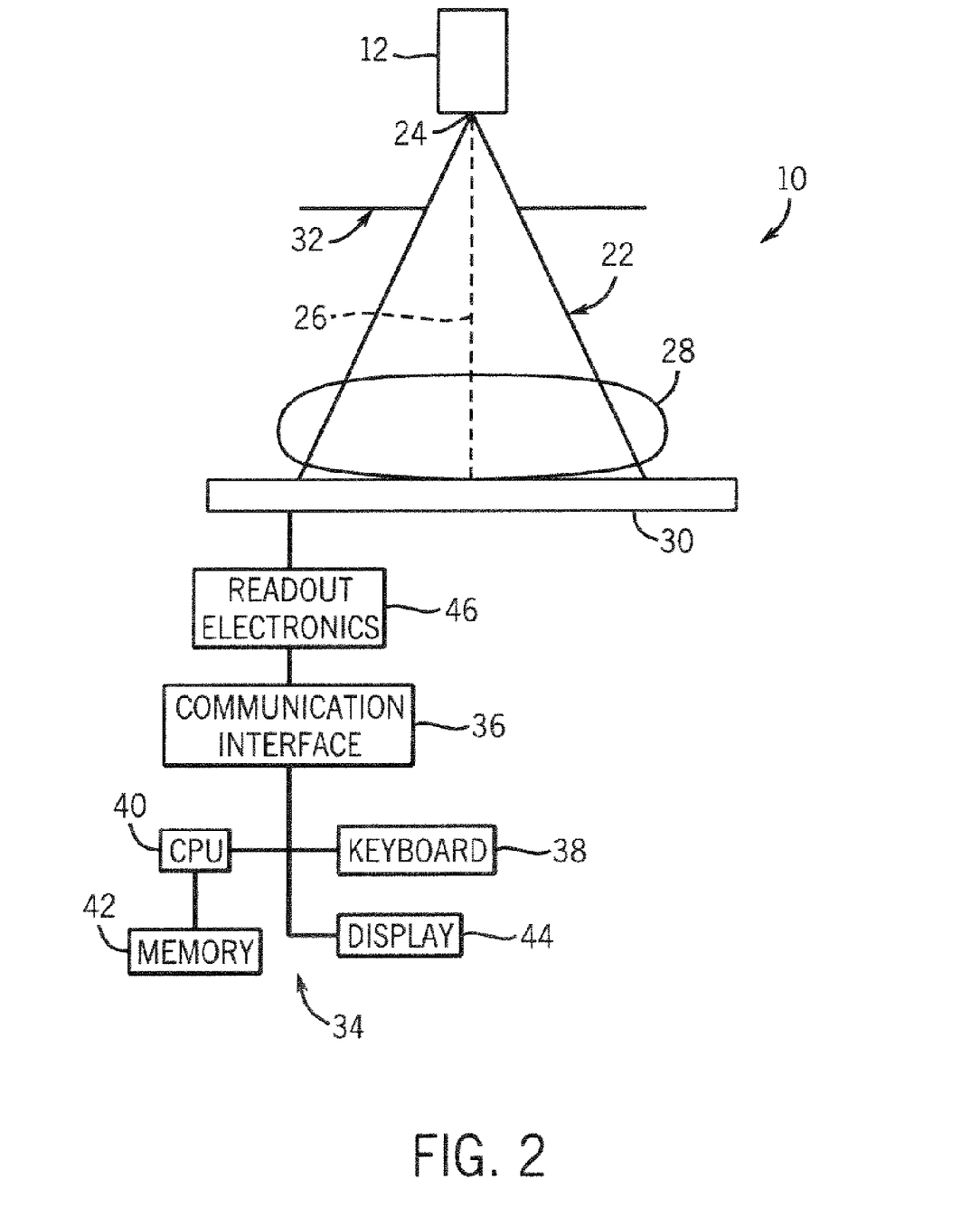
FIG. 2 is a schematic block diagram of the exemplary x-ray imaging system shown in FIG. 1.

Referring now to FIG. 2, a schematic of x-ray imaging system 10 is illustrated. As referenced above, system 10 includes x-ray source 12 designed to project a fan bean of irradiation 22 from focal spot 24 along axis 26 toward an object to be imaged 28. One skilled in the art will appreciate that medical patients as well as luggage, packages, and the like may be non-invasively inspected using the exemplary x-ray imaging system 10. A flat panel digital detector 30 detects x-rays passing through and attenuated by object 28. A collimator assembly 32, schematically shown in FIG. 2 as comprising collimator blades, may be used to collimate the x-ray fan beam 22 to control the scope of irradiation.

A host or scanner interface 34 includes a communication interface 36, a keyboard 38 or other data entry device, a CPU 40, memory 42, and a display unit 44, such a computer monitor, to display reconstructed images of the object. A bus connects the keyboard 38, CPU 40, memory 42, and display unit 44 to the communication interface 36. The CPU may include a microprocessor, digital signal processor, microcontroller, as well as other devices designed to carry out logic and processing operations. Signals corresponding to an x-ray image are read out from flat panel detector 30 via readout electronics 46. While not shown, it is contemplated that the host interface 34 may be connected to a centralized facility via the Internet or communications link for monitoring and maintenance.

Additionally, the readout electronics may read out signals from the flat panel detector across a tethered connection between the detector and the imaging system. It is also contemplated that read out may be achieved across a wireless communication between the detector and imaging system. In this regard, one skilled in the art will appreciate that the imaging system and detector may be equipped with transceivers, antennas, and other operational circuitry to support the wireless transmission of data.

Figure 3:
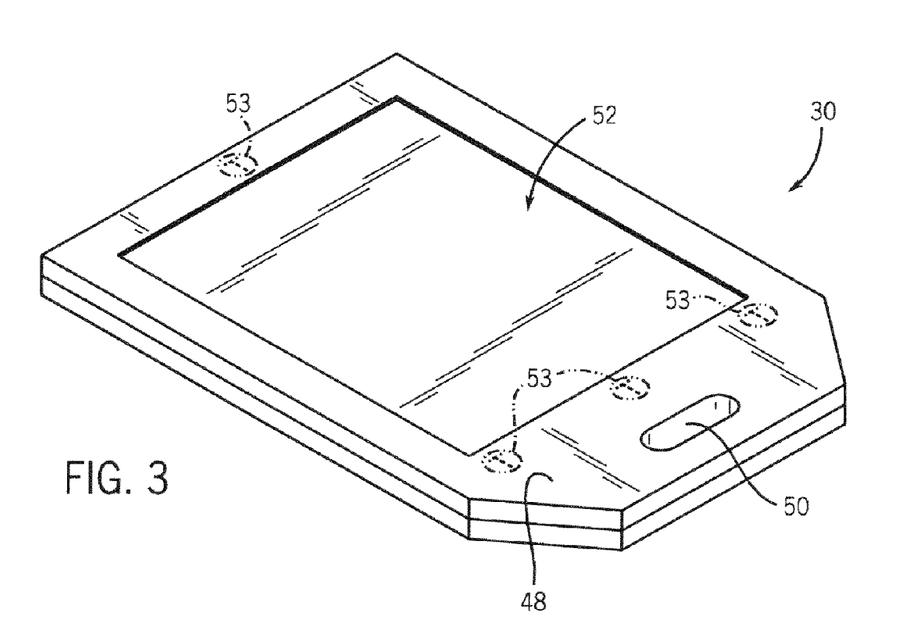
FIG. 3 is a perspective view of a portable, solid-state, flat panel, digital x-ray detector incorporating the present invention.

Referring now to FIG. 3, a perspective view illustrates a portable, flat panel x-ray detector 30 incorporating the present invention. Detector 30 is preferably an indirect detection, solid-state, digital detector that determines x-ray attenuation through an imaging subject from the emission of light by a scintillator that emits light upon the incidence of x-rays. The detector 30 includes a cover 48 formed of lightweight, durable composite material. A handle 50 is incorporated into the cover to support the portability of the detector. As shown, the detector 30 may be constructed without a fixed tether. In this regard, the detector may be connected to a tether (not shown), which is connected to the readout electronics when in use. When not in use, the detector may be easily detached from tether and stored remotely from the imaging system. The top of the cover includes a template 52 that visually defines the surface dimensions of the scintillator layer in the detector. Template 52 is designed to visually assist a user in positioning of the detector for data acquisition.

As will be described in greater detail below, thermal sensors 53, e.g. thermistors, may be integrated within cover 48 to provide temperature feedback regarding the temperature of the x-ray detector during data acquisition. Preferably, the temperature sensors 53 are positioned at pre-defined "hot spots" that have greater sensitivity to temperature variations in the internal volume of the x-ray detector. In this regard, the x-ray detector can be removed from use if a temperature limit is exceeded, e.g. greater than 41 degrees Celsius. The temperature data can also be used to select an appropriate calibration map for calibrating the x-ray detector or correcting acquired attenuation data as detector performance varies with temperature.

While the present invention is particularly applicable with indirect detection digital detectors, the present invention may also be implemented with direct detection digital detectors. Direct detection digital detectors utilize a layer of amorphous selenium or similar material photoconductor coupled to a thin film transistor array. X-ray interaction in the selenium layer releases electrons (or electron holes), which are used to form signal directly. An electrode is often used to create an electric field across the selenium layer to minimize the lateral spread of electrons, preserving spatial resolution. In addition to selenium, mercuric iodide, cadmium telluride, and lead iodide may be used.

Figure 4:
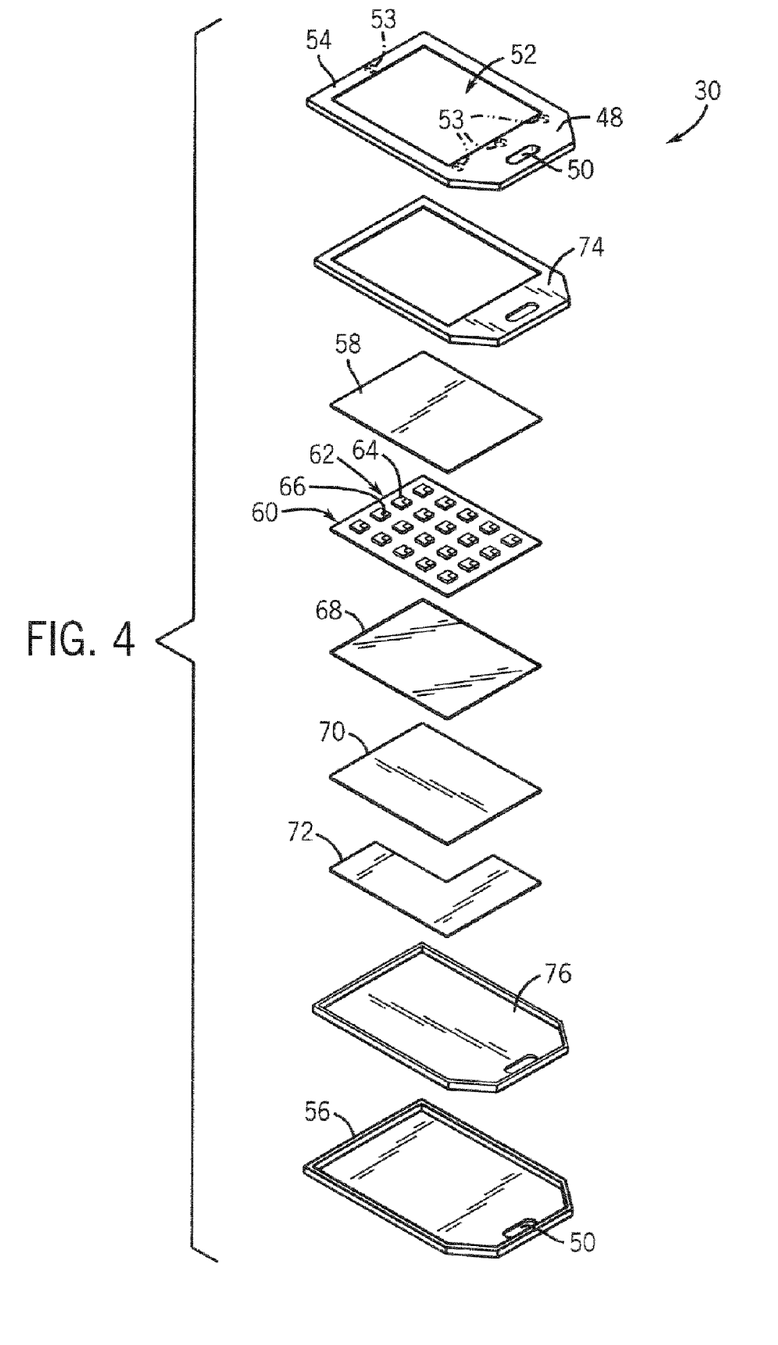
FIG. 4 is an exploded view of the x-ray detector shown in FIG. 3.

Referring now to FIG. 4, an exploded view schematically illustrates the internal composition of detector 30. Detector 30 includes a top cover 54 that along with base cover 56 provides a shell or enclosure for its internal components. Both covers 54, 56 are preferably formed of a composite material, such as carbon graphite, and impact-absorbing material, such as viscoelastic foam, so as to house and protect the detector components from fracture when exposed to a load or dropped. As will be described in greater detail below, covers 54 and 56 may be constructed with bumpers, foam inserts, layers of impact absorbing material, and the like to inhibit fracturing of the detector components when dropped or exposed to a load. When assembled, the top cover 54 is constructed in such a manner that the detector may be placed on a floor and support a standing subject. In this regard, the top cover panel 54 is designed to minimally deflect when subjected to a load.

Top cover 54 and base cover 56 collectively form handle 50 when assembled. The handle supports portability of the detector. Additionally, the detector is constructed to be quickly detached from a tether (not shown) that is used to connect the detector to the scanner during data acquisition and readout. As such, detector 30 may be transported to and from multiple scan stations remote from one another. This is particularly advantageous for emergency rooms and other triage facilities. Further, the portability and detachability of the detector further enhances the mobility of a mobile x-ray imaging system, such as that shown in FIG. 1.

Detector 30 further includes a scintillator layer 58 designed to convert incident x-rays or gamma rays to visible light. Scintillator layer 58, which may be fabricated from CsI or other scintillating material, is designed to emit light proportional to the number and energy of the x-rays received. As such, light emissions will be higher in those regions of the scintillator layer 58 where either more x-rays were received or the energy level of the received x-rays was higher. Since the composition of the subject will attenuate the x-rays projected by the x-ray tube, the energy level of the x-rays impinging upon the scintillator layer will not be uniform across the scintillator layer. This variation in light emission will be used to capture contrast in the reconstructed image.

The light emitted by the scintillator layer 58 is detected by detector elements of a detector element array 60. Each detector element 62 corresponds to a picture element or pixel in the reconstructed image. Each detector element 62 includes a light sensitive or photoconductive region 64 and an electronics region 66. During exposure to x-rays, electrons are released in the light sensitive region 64 in proportion to the light detected in the region 64. The electronics region 66 includes a capacitor (not shown) that stores the electrical charge accumulated by the light sensitive region. After exposure, a thin-film-transistor (not shown) in the electronics region 66 is biased so as to connect the capacitor to readout electronics. Generally, a multiplexer (not shown) is used to control read out of the discrete detector elements in a sequential, raster fashion. In this regard, the output of each detector element is sequentially input to a digitizer for digitization for subsequent image reconstruction.

The thin-film-transistors of the detector elements 62 are supported by a glass substrate 68. Lead lines (not shown) etched in substrate 68 are used for routing of the electrical output of the detector elements as well as applying the biasing voltages to the thin-film-transistors. The glass substrate is generally very thin and fragile. In this regard, as referenced above, the top cover and base cover 54 and 56 are designed with impact absorbing material to help prevent fracturing of the glass substrate. Additionally, as the detector 30 may be used to support a relatively large load during imaging, e.g. imaging of the feet of an average sized adult male, the top cover panel 54 is further designed to reduce the stress on the detector to further prevent fracturing of the glass substrate and other detector components.

The glass substrate 68 is supported by a detector panel support 70. Panel support 70 is not only designed to support substrate 68, but is also used to separate the x-ray conversion and light detection components from the electronics 72. Panel support 70 is constructed to include radiation absorbing material in addition to structurally supporting material. Incorporating radiation absorbing material within the panel support reduces or eliminates the detection of backscattered x-rays. That is, the radiation absorbing material absorbs x-rays passing through the scintillator layer, detector element array, and glass substrate, as well as x-rays that deflect off the back cover of the detector. In this regard, the electronics 72 are not imaged.

Electronics 72, in one embodiment, have an L-shape and is disposed to support the processing and logic control electronics of the detector. The electronics preferably includes LEDs for monitoring operation and diagnostics of the detector, such as temperature sensors 53. The electronics may also support an accelerometer designed to detect acceleration of the detector and store data accordingly. In this regard, the accelerometer may be used to record the date and time when the detector experienced dramatic increases in acceleration, i.e. when dropped. The electronics may also include various storage devices including flash storage. In a wireless implementation, the motherboard may include an antenna and transceiver for wirelessly transmitting data to the x-ray scanner. Additionally, the electronics may include a battery or other DC power source for powering the detector electronics. The electronics are supported by base cover panel 56.

As described above, the x-ray detector is designed to withstand relatively high-energy impacts, stresses, and strains such that the relatively sensitive components, i.e. scintillator layer, detector element array, glass substrate, and motherboard, are not damaged when the detector is dropped or stepped upon. In this regard, in one embodiment, the x-ray detector 30 includes two layers of impact-absorbing material 74, 76. One layer 74 is sealed against or otherwise placed in proximity to the undersurface of top cover panel 54 so as to be sandwiched between the top cover panel and scintillator layer 58. The other layer 76 is sealed or otherwise placed in proximity to the top surface of base panel 56 so as to be sandwiched between motherboard 72 and base panel 56. While two impact-absorbing layers 74, 76 are shown, it is contemplated that the detector may include only a single layer which is preferably sealed against the undersurface of top cover panel 54 or multiple layers interstitially disposed between the detector components. In this regard, the impact-absorbing material is designed not to attenuate radiation and, as such, does not interfere with data acquisition.

The impact-absorbing material is preferably a viscoelastic material that is designed to absorb the shock and vibrations placed on the detector when dropped but also deflect the force placed on the detector when stepped upon or otherwise subjected to a load, e.g. a standing patient for a foot/feet scan. In this regard, the impact absorbing material will deform when subjected to a load, but also recover its shape when the load is removed. As such, the impact-absorbing material has a memory.

The viscoelastic material, which may be foam or other plastic, is designed to deflect and absorb stresses and strains on the detector. As such, when the detector is stepped upon or dropped, the internal components of the detector, e.g. scintillator layer, detector element array, glass substrate, and motherboard, do not fracture or are otherwise damaged. One skilled in the art will appreciate that the thickness, density and composition of the impact-absorbing material may be variably selected to define the limits by which the detector may be subjected to a load or dropped without damage to the detector components. Preferably, however, the detector should have sufficient impact absorbing material such that the damage does not result when the detector is dropped a distance of 20 cm. and/or subjected to a point-load of 370 lbs.

Further, it is contemplated that layers 74 and 76 can have similar or dissimilar thicknesses, and be composed of similar or dissimilar impact absorbing material(s). For example, layer 74 may be designed to be more absorbent and deflective than layer 76. In this regard, layer 74 may be thicker than layer 76 or formed from material with improved absorption and deflective characteristics. Additionally, layer 74 may be formed of foam having pronounced viscoelastic properties whereas layer 76 is formed of a polycarbonate, PVC, or other material with less pronounced viscoelastic characteristics.

Figure 5:
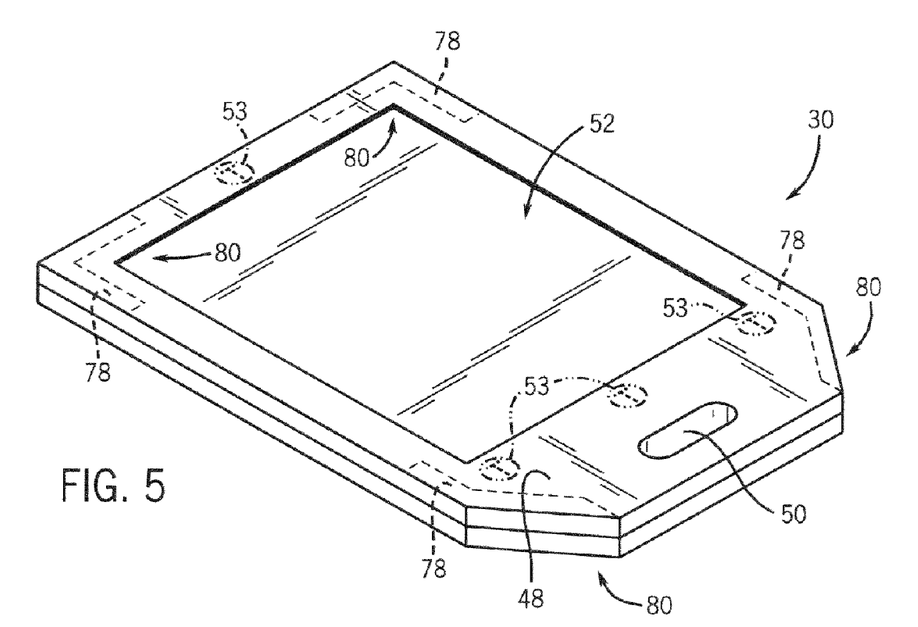
FIG. 5 is a perspective view of a portable, solid-state, flat panel, digital x-ray detector according to another embodiment of the present invention.

Referring now to FIG. 5, it is contemplated that the x-ray detector 30 may be constructed to have impact-absorbing inserts 78 placed in cavities positioned internally about the perimeter of the x-ray detector cover 48. The inserts may be positioned internally about the entire perimeter of the detector cover or, as illustrated in FIG. 5, positioned at identified impact zones 80. For example, inserts 78 may be positioned at each corner of the detector 30. Accordingly, when dropped, the detector is more likely to impact a floor or other surface at a corner. It is recognized that the detector may be constructed that its weight distribution increases the likelihood that that detector will impact the floor or other surface at a corner when dropped. By incorporating impact-absorbing material at the corners of the cover 48, the shock and resulting vibrations of the drop incident may be absorbed by the insert 78 and prevented from transferring to the internal components of the detector. It is recognized that the entirety of the shock may not be absorbed or otherwise deflected, but a sufficient percentage of the shock is absorbed such that any shock or vibration experienced by the internal components is of a magnitude insufficient to cause damage to the internal components. Additionally, by incorporating the inserts internally within the detector, the overall size and weight of the detector is negligibly increased, if any.

It is contemplated that the inserts 78 may be used in conjunction with a layer of impact-absorbing material positioned between the top cover and base panels and the internal components of the detector, such as that shown and described with respect to FIG. 4. In this regard, the layers of impact-absorbing material may be fabricated from materials with better deflective properties than impact absorption properties. On the other hand, the inserts 78 may be fabricated from materials having better impact absorption properties than deflective properties. As a result of this construction, the detector is able to handle greater point loads and greater impacts than that achieved with inserts or layers of impact absorbing material alone.

Figure 6:
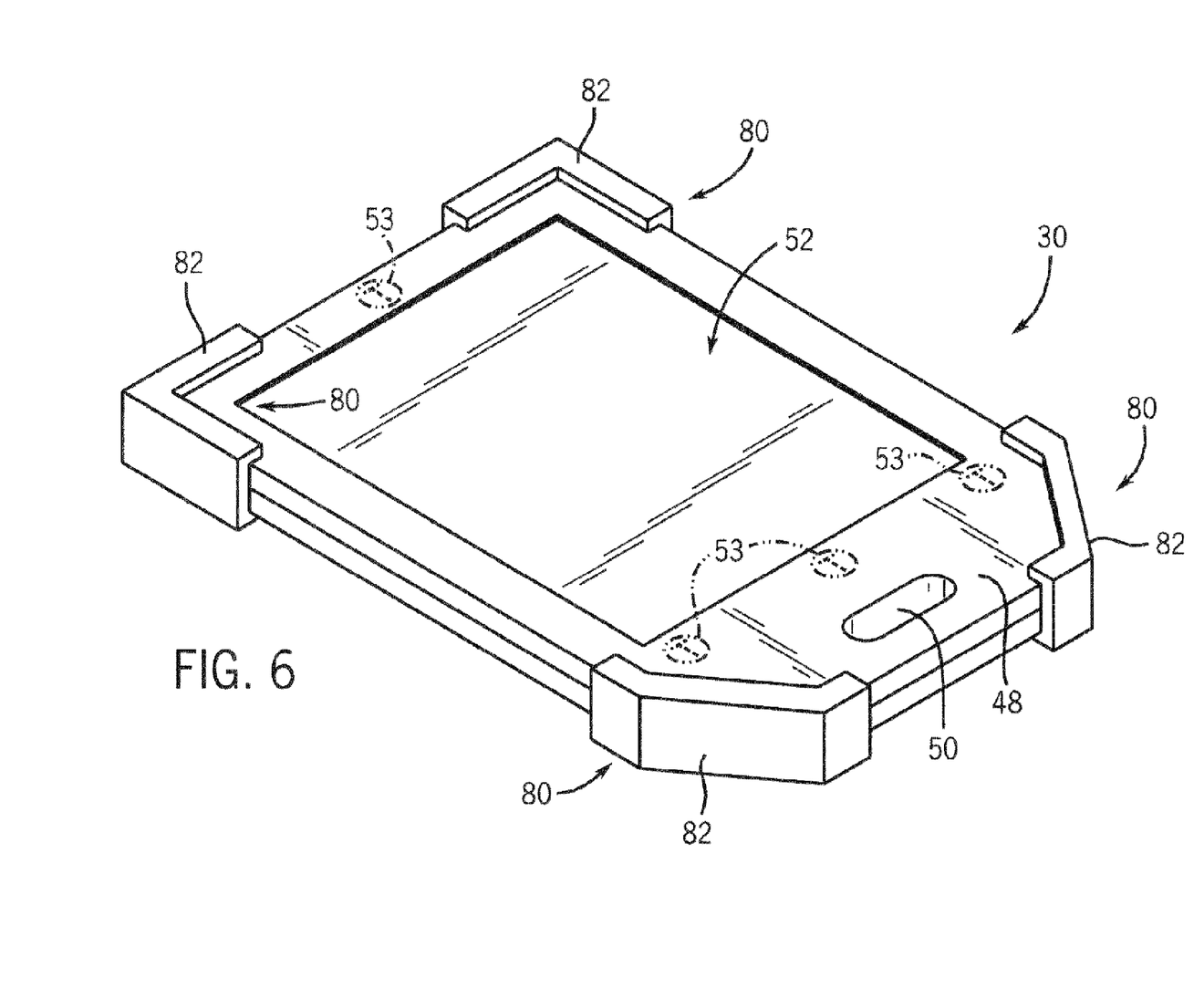
FIG. 6 is a perspective view of a portable, solid-state, flat panel, digital x-ray detector according to yet another embodiment of the present invention.

It is also contemplated that "bumpers" of impact-absorbing material may be secured, sealed, or otherwise connected to the external perimeter of the x-ray detector cover. This embodiment is illustrated in FIG. 6. As shown, bumpers 82 of impact absorbing material may be sealed against one or more corners of the detector cover 48. As the corners are identified as impact zones, the bumpers are shown at each corner. It is recognized that other impact zones may be identified around the perimeter of the cover 48 and, as such, receive a bumper. In this regard, it is contemplated that a continuous bumper may be sealed against the entire perimeter of the cover 48. In contrast to the embodiments described with respect to FIGS. 4 and 5, the bumpers 82 shown in FIG. 6 may increase the size of the detector. On the other hand, it is contemplated that the corners of the cover 48 may be replaced with bumpers 82 so as to not increase the size of the detector.

For instance, the cover 48 may be molded in such a manner that impact-absorbing material is used at the corners rather than the composite material used throughout the remainder of the cover. Or, cover 48 may be initially constructed without corners whereupon properly shaped wedges of impact-absorbing material may be glued or otherwise sealed to the cover so as to fill in the voids defined at the corners. Further, similar to the embodiment illustrated in FIG. 5, the detector of FIG. 6 may be constructed to include impact-absorbing material at selected impact zones as well as layers of impact-absorbing material such as that shown in FIG. 4.

During the image reconstruction process, acquired x-ray imaging data is typically subjected to a number of calibration and corrective processes to improve image quality. These calibration and corrective measures typically include a gain correction, a conversion factor calibration, and a bad pixel correction. These measures, as well as others, as set forth above, presume an x-ray detector temperature during the data acquisition process. More particularly, these calibration and corrective measures presume that the temperature of the x-ray detector is within a given temperature range, e.g. 25-35 degrees Celsius. However, it is possible for the x-ray detector to have a temperature outside the desired temperature range which affects the fidelity of an applied calibration and corrective measure. Moreover, by not applying a corrective or calibration measure for a specific temperature, the application of a particular calibration or correction may be less than optimal notwithstanding the x-ray detector having a temperature within a desired temperature range during data acquisition. In short, since x-ray detector performance varies with temperature so does the accuracy and precision of an applied correction or calibration.

Figure 7:
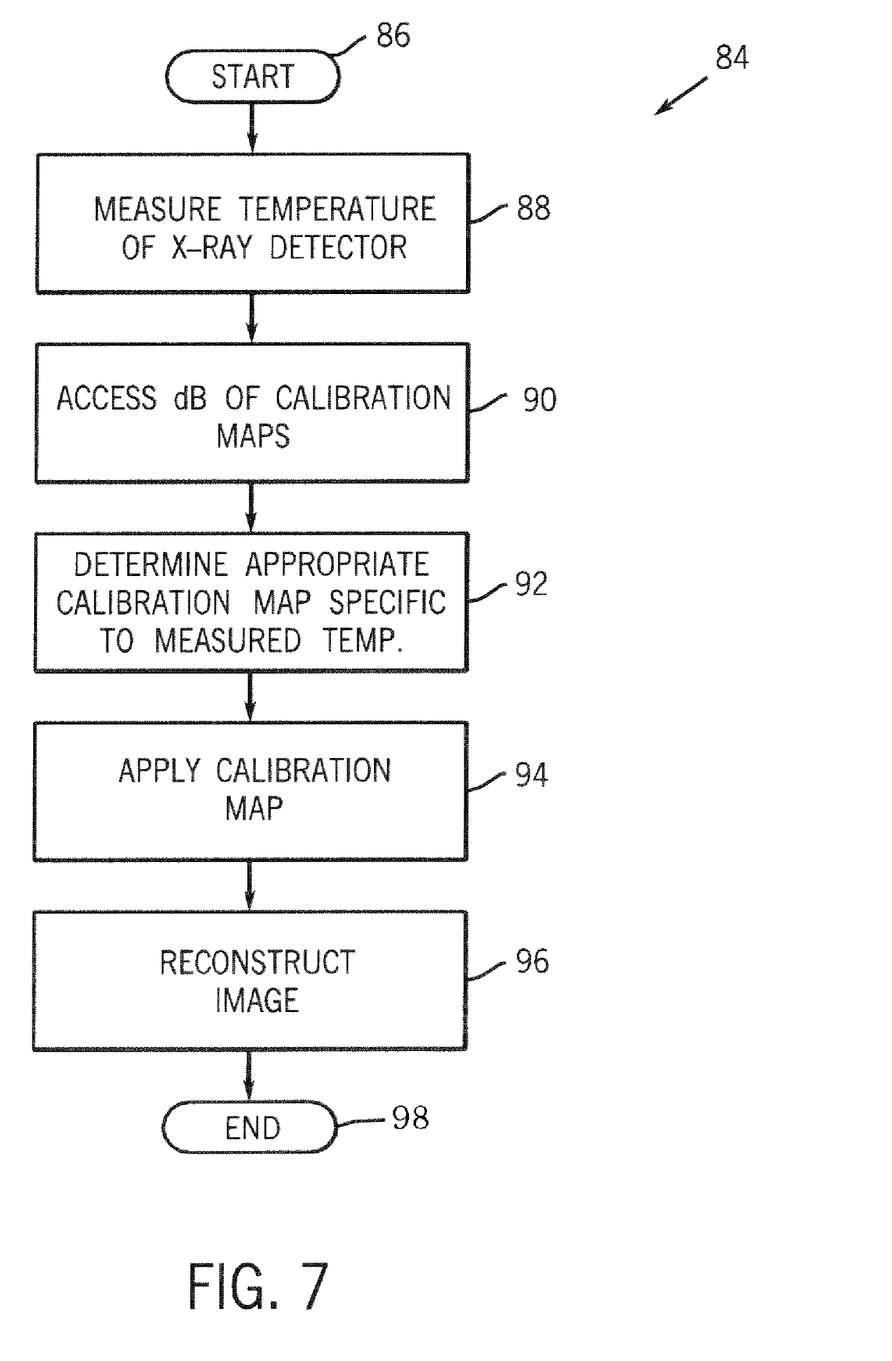
FIG. 7 is a flow chart setting forth the steps of temperature-dependent calibration selection process according the present invention.

Referring now to FIG. 7, the steps of a high level temperature-sensitive data correction technique 84 are set forth. Technique 84 begins at 86 with the accessing of stored x-ray imaging data from a computerized archival location or the real-time acquisition of raw imaging data. If archived data is accessed, the data will be coded with temperature data indicating the temperature of the x-ray detector during data acquisition. If imaging data is acquired in real-time, then the temperature of the x-ray detector during the imaging data acquisition will be measured 88 from one or more temperature sensors in the x-ray detector. In one embodiment, the temperature sensors are embedded at pre-defined hot spots in the cover of the detector. The temperature sensors are designed to measure the temperature of the cover or internal volume of the detector. From this temperature data it is possible to extrapolate or otherwise determine the temperature of the detector substrate during data acquisition. Based on the feedback of the temperature sensors (in the case of multiple sensors, an average of the readings is used), a database of calibration maps is accessed 90 and an appropriate calibration map is identified or otherwise determined. 92. Preferably, the database includes a calibration map that is specific for the measured temperature. Otherwise, an interpolation may be carried out between two or more calibration maps to determine the parameters of a calibration map optimal for the measured temperature. Once the appropriate calibration map is selected or determined, the map is applied in a conventional manner 94 to the acquired imaging data. An image is then reconstructed 96 whereupon the process is complete 98.

Figure 8:
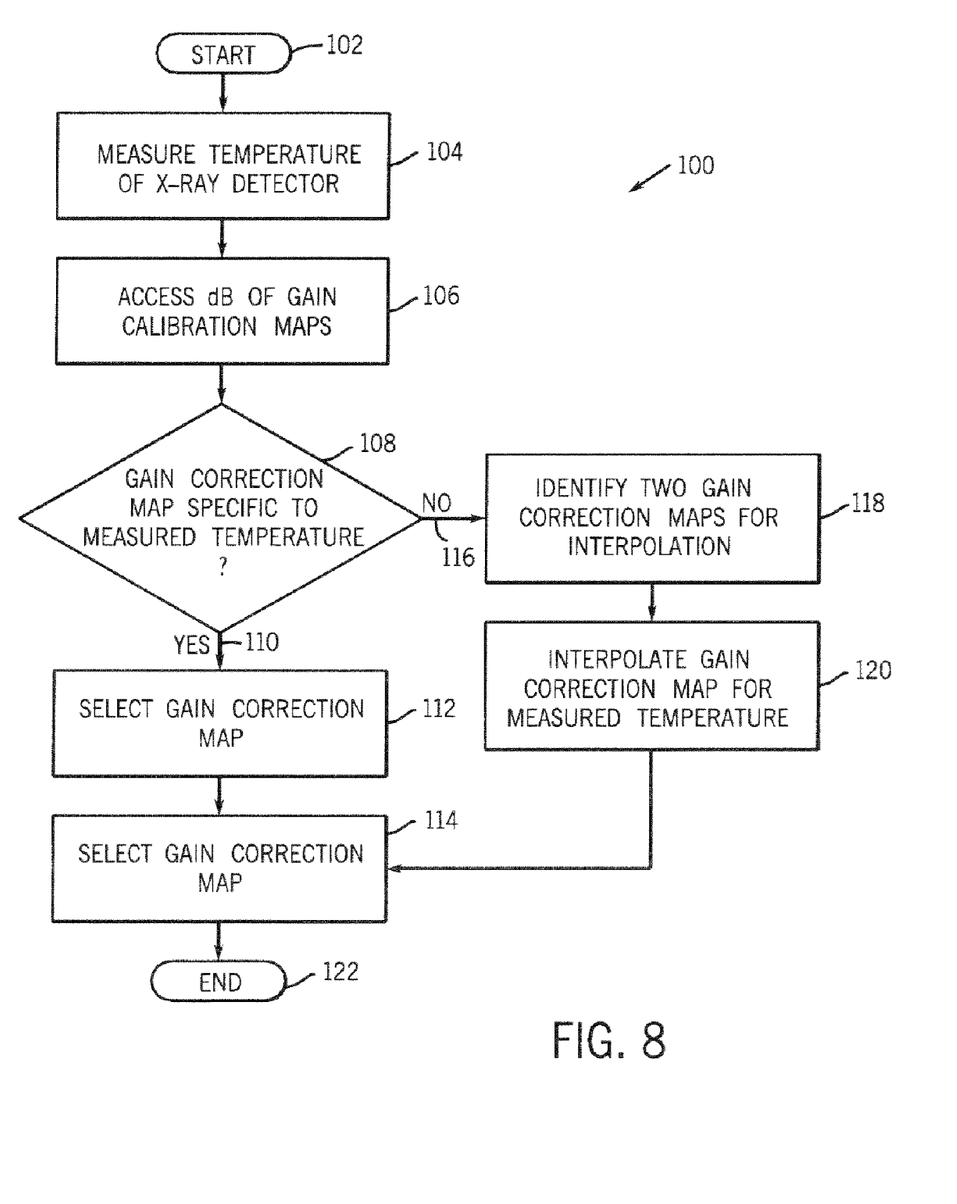
FIG. 8 is a flow chart setting forth the steps of selecting a gain calibration map appropriate for a specific x-ray detector temperature during data acquisition according to the present invention.

The present invention may be applied to identify an appropriate calibration or corrective measure for a number of calibrations or corrections. For example, as shown in FIG. 8, the present invention may be used to determine an appropriate gain calibration map. In this regard, the identification technique 100 begins at 102 with the acquisition of imaging data or accessing of archived imaging data. The temperature of the x-ray detector during data acquisition is measured at 104 or determined from the coded archived imaging data. A database of temperature-marked gain calibration maps is then accessed at 106. The database is then analyzed to determine if there is a stored map specific to the temperature of the x-ray detector measured during data acquisition 108. If so 108, 110, the appropriate gain calibration map is selected 112 and applied 114. If not 108, 116, a bicubic or other interpolation is carried out to determine the values of a gain correction map. In one embodiment, two gain correction maps are identified 118 and used for interpolation 120. The interpolation process yields values of a gain calibration map that is applied at 114 to reduce artifacts in the imaging data. An image is then reconstructed and the technique is complete at 122.

For instance, if the temperature of the x-ray detector during the acquisition of imaging data is measured to be 36 degrees Celsius, the gain correction map database will be inspected to determine if the database has a 36 degree Celsius gain correction map. If so, that map will be used. If not, an interpolation process is preferably undertaken. That is, two gain correction maps will be selected and their corresponding data values will be used to establish the values of a gain calibration map for 36 degrees Celsius. Preferably, the maps selected for interpolation correspond to temperatures that are the closest to the measured temperature and book-end the measured temperature. For example, if the database has a 33 degrees Celsius map, a 35 degrees Celsius map, and a 38 degrees Celsius map, the 35 and 38 degrees Celsius maps would be used for interpolation of a 36 degree Celsius given map.

It is also contemplated however that the gain calibration map corresponding to a temperature closest to the measured temperature may be used instead of carrying out an interpolation process. In this regard, for the example given above, the 35 degrees Celsius gain calibration map would be selected and applied to reduce artifacts in a reconstructed image.

Another corrective measure generally applied to acquired data is called "bad pixel" correction. This corrective measure is typically used to identify those pixels (detector elements) that are presumed to have corrupted data. Bad pixels may result because of poor connectivity, poor dynamic range, poor SNR characteristics, as well as poor linearity in their response. Generally, the number of bad pixels of an x-ray detector increases with temperature. However, this variability is typically not considered in bad pixel calibrations.

For example, the bad pixel map for a given x-ray detector may presume that x-ray data is acquired at 35 degrees Celsius. At that temperature, a number of bad pixels are presumed corrupted and the data from those pixels is ignored during the reconstruction process. However, it is possible for a pixel that is bad at 35 degrees Celsius to not be bad at 25 degrees Celsius. As a result, when data is acquired with the detector at 25 degrees Celsius, data is ignored and image quality is affected. As such, the present invention also includes the creation of several temperature-dependent bad pixel maps that can be stored in a database or otherwise archived and selectively accessed based on the temperature of the detector during data acquisition.

Figure 9:
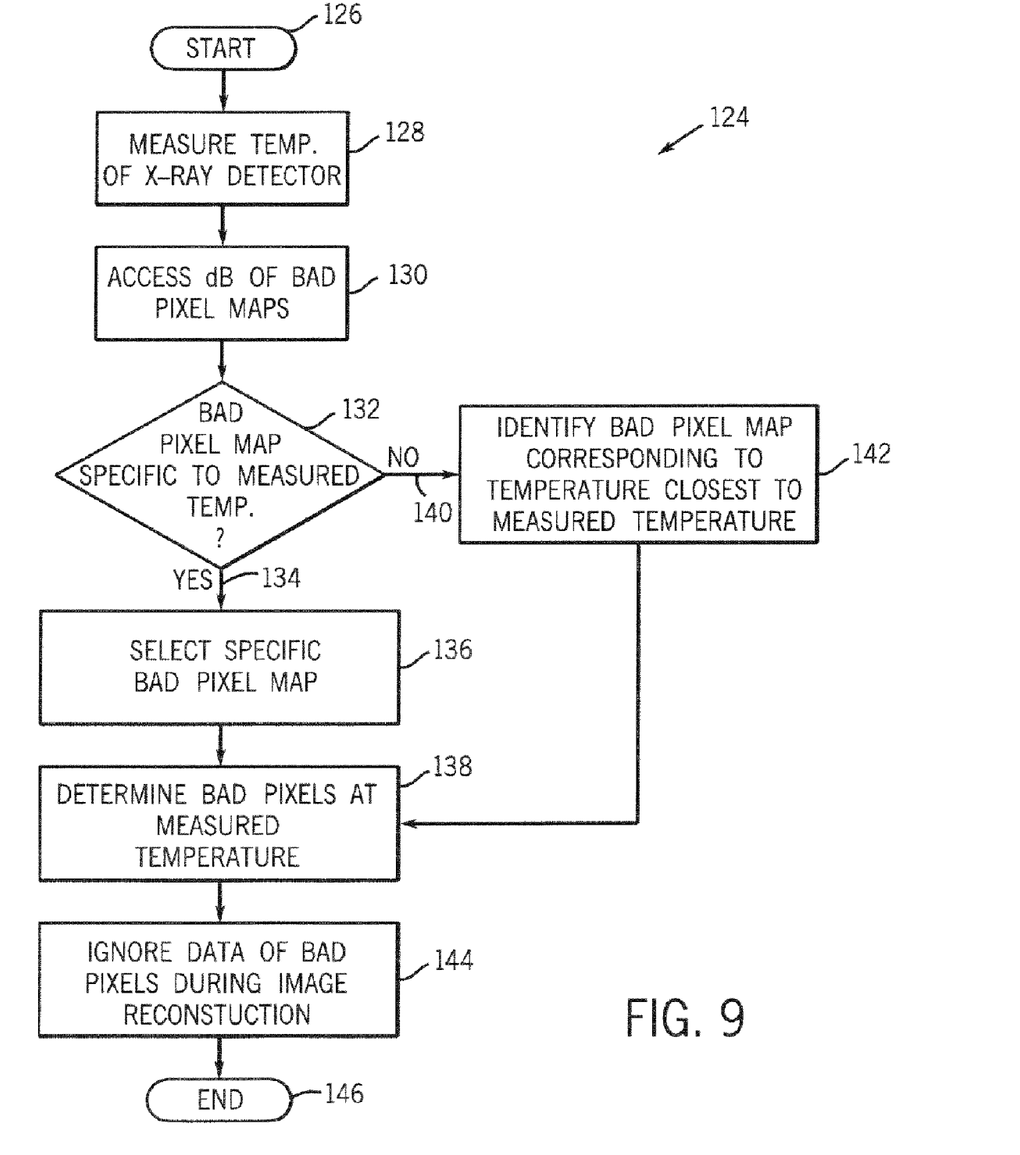
FIG. 9 is a flow chart setting forth the steps of selecting a bad pixel calibration map appropriate for a specific x-ray detector temperature during data acquisition according to the present invention.

Referring now to FIG. 9, a bad pixel calibration technique according to the present invention is illustrated. This technique 124 begins at 126 with the acquisition or otherwise accessing of x-ray imaging data. Thereafter, the temperature of the x-ray detector during the acquisition of the x-ray imaging data is determined at 128, whether in real-time with the acquisition of the imaging data, or from encoding of the archived data. A database of bad pixel maps is then accessed at 130. Initially, a determination is made as to whether the database includes a bad pixel map specific to the measured x-ray detector temperature 132. If so 132, 134, the corresponding bad pixel map is selected 136 and applied at 138 to determine those pixels presumed to be bad at the measured temperature. If not 132, 140, a bad pixel map for a corresponding temperature closest to the measured temperature of the x-ray detector is identified 142. It is contemplated that the identified bad pixel map may over-estimate or under-estimate the pixels presumed to be bad. Once the bad pixels have been identified at 138 based on the applied bad pixel map, the data for the presumed bad pixels is then ignored during the reconstruction process 144. The technique then ends at 146 with image reconstruction.

Another corrective measure that is routinely carried out during x-ray image reconstruction is conversion factor correction. Generally, the x-ray imaging data is modified by a conversion factor to affect the brightness of the reconstructed image. More particularly, an x-ray detector's conversion factor provides an indication of that detector's sensitivity. Conventional conversion factor corrections have presumed that the data is acquired when the x-ray detector is at a particular temperature or within a given temperature range. However, this parameter also varies with temperature. Accordingly, if the x-ray detector temperature during data acquisition differs from the presumed temperature, the conversion factor may be less than ideal.

Figure 10:
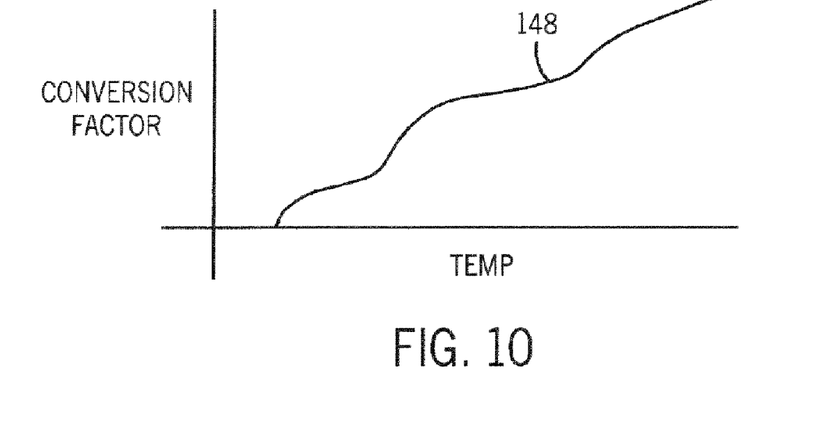
FIG. 10 is a graph illustrating an exemplary conversion factor curve for an exemplary x-ray detector.

As such, the present invention includes generation of a conversion factor curve that is a function of temperature for a given x-ray detector that can be analyzed to determine an appropriate conversion factor for a given detector temperature. An exemplary conversion factor curve is illustrated in FIG. 10. As shown in curve 148, the conversion factor varies as the temperature of the x-ray detector during data acquisition varies. Moreover, it is possible for an x-ray detector to be characterized by a conversion factor curve that yields drastic differences in conversion factors across a given temperature range. As such, FIG. 10 illustrates that there is a need to have specificity in conversion factor determinations.

Figure 11:
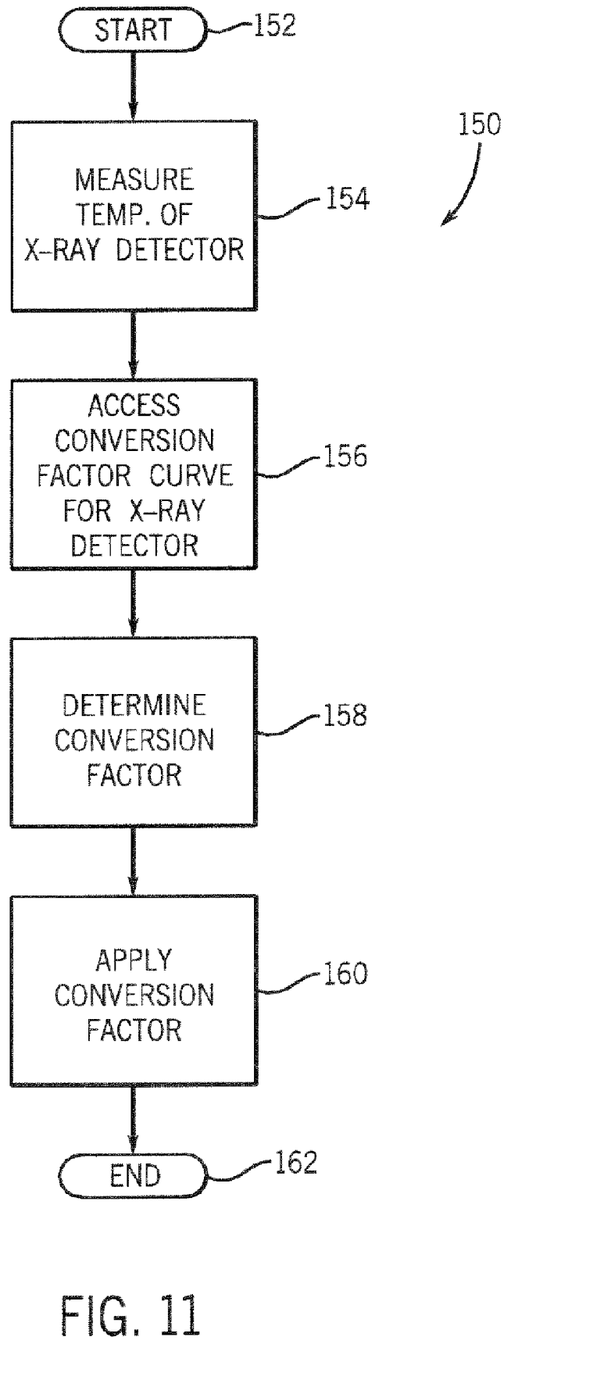
FIG. 11 is a flow chart setting forth the steps of selecting a conversion factor appropriate for a specific x-ray detector temperature during data acquisition according to the present invention.

Accordingly, as shown in FIG. 11, the present invention includes a technique 150 for determining an appropriate conversion factor. Specifically, the calibration technique 150 begins at 152 with acquisition of imaging data. The temperature of the x-ray detector during the data acquisition is then determined at 154. A conversion factor curve specific to the x-ray detector used to acquire the imaging data is then accessed at 156. The curve, such as that illustrated in FIG. 10, is then analyzed to determine the conversion factor that corresponds to the measured x-ray detector temperature 158. Once the appropriate conversion factor is determined, the conversion factor is applied at 160 in a conventional manner whereupon the calibration process ends 162.

Another common calibration technique is generally referred to as "offset" calibration. In offset calibration, an offset or dark image is used to remove artifacts in acquired imaging data. Offset artifacts are artifacts that are not x-ray dependent. As such, the acquisition of offset data occurs without x-rays. In this regard, when subtracted from imaging data, artifacts not attributable to x-rays will be removed from the imaging data and thus not appear in the reconstructed image.

Ideally, the offset data would be acquired simultaneously with the imaging data; however, this simultaneous acquisition is not feasible as the offset data must be acquired without x-rays. As such, as illustrated in FIG. 12, there is a time delay between the acquisition of x-ray imaging data and offset imaging data.

Figure 12:
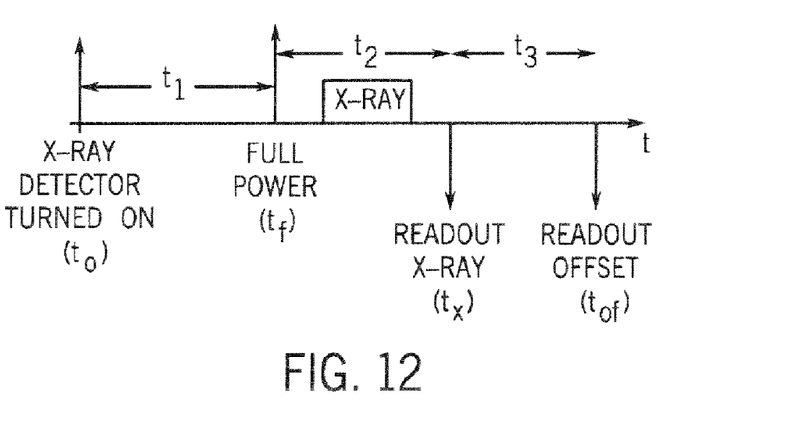
FIG. 12 is a timing diagram illustrating the acquisition of x-ray imaging and x-ray offset data.

FIG. 12 illustrates a timing diagram for a typical x-ray imaging session. At to the x-ray detector, presumed to be in an OFF state, is turned ON. Once turned ON the x-ray detector warms up during $t_1$ to a FULL POWER state, $t_f$. Preferably, x-ray imaging data is not acquired until the detector is in the FULL POWER state. As such, x-ray imaging takes place during X-RAY state whereupon the acquired x-ray attenuation data is readout at $t_x$. The time interval between the detector reaching FULL POWER and the readout of the attenuation data is defined $t_2$. Following the readout of the x-ray imaging data and without the projection of x-rays, offset data is readout at $t_{of}$. The time interval between x-ray imaging data readout and offset data readout is defined as $t_3$.

Because there is the delay between the acquisition of imaging and offset data, power transients can often induce artifacts in the offset data that are not found in the imaging data, and vice-versa. That is, the powering up of the x-ray detector typically induces "power mode" transients. These transients can cause artifacts to occur in the acquired data. Moreover, these transients vary over time and, as such, the impact of these transients can appear in the imaging data differently than in the offset data. More particularly, if the transients-induced artifacts are not of the same magnitude in the offset and imaging data, the subtraction of the offset data from the imaging data will not remove them. This is illustrated in FIG. 13.

Figure 13:
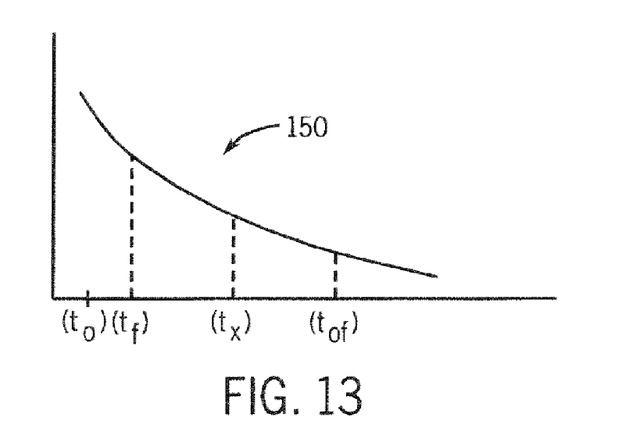
FIG. 13 is a curve illustrating an exemplary power transients curve for an exemplary x-ray imaging data and x-ray offset data acquisition.

FIG. 13 is a graph illustrating a power mode transient curve 150 for an exemplary x-ray detector. In the exemplary curve 150, the magnitude of the transients decreases with time. As such, the magnitude of the transients at $t_x$ is larger than at $t_{of}$. As a result, the impact of the transients will be less pronounced in the offset data than in the imaging data. Therefore, when the offset data is subtracted from the imaging data, residual artifacts will result. In this regard, curve 150 can also be examined to determine what the difference in the magnitude of those transients will be by measuring the time interval between imaging data acquisition and offset data acquisition. The offset data can then be augmented so that the magnitude of the power mode transients' artifacts can be artificially matched to that of the imaging data. When the offset data is then subtracted from the imaging data, the artifacts associated with power mode transients between the acquisition of imaging data and offset data are reduced.

The present invention has been described with respect to a number of calibration and/or corrective processes. One skilled in the art will appreciate that all of the calibration and corrective measures can be carried out independent of one another. Moreover, the acquired imaging data may be subject to one or more of the calibration/corrective techniques described herein.

Therefore, the present invention includes an x-ray imaging system having an x-ray detector configured to detect radiation attenuation through a subject to be imaged and output imaging data in response thereto and at least one thermal sensor configured to sense a temperature of the x-ray detector and provide temperature feedback of the x-ray detector. The system further has a processor operationally connected to receive the temperature feedback from the at least one thermal sensor and apply a correction to the output of the x-ray detector specific to the temperature of the x-ray detector.

An x-ray detector is disclosed that includes a scintillator configured to emit light in response to reception of radiation and a detector element array configured to output radiographic data and having a plurality of detector elements. Each detector element is configured to detect light from the scintillator and provide an electrical signal that may be processed for image reconstruction. The x-ray detector also has a temperature sensor to provide feedback as to temperature of the x-ray detector and a processor programmed to calibrate the radiographic data output by the detector element array specific to the temperature of the detector element array during radiographic data acquisition.

The invention is also directed to a method of x-ray detector calibration. The method includes determining a temperature of an x-ray detector during data acquisition from a subject to be imaged and selecting a data correction map specific to the temperature of the x-ray detector from a number of stored data correction maps. The selected data correction map is then applied to data acquired by the x-ray detector to reduce artifacts in an image reconstructed from the data acquired by the x-ray detector.

A method of x-ray data correction is presented that includes the steps of acquiring radiographic data from a subject to be imaged and determining a temperature of an x-ray detector used to acquire the radiographic data. The method also includes the steps of comparing the temperature of the x-ray detector to a temperature-dependent calibration map and identifying those detector elements of the x-ray detector that are presumed corrupted at the temperature of the x-ray detector during data acquisition. The method then ignores data acquired by those detector elements presumed corrupted during image reconstruction.

A method of x-ray data correction is presented that is defined by acquiring radiographic data from a subject to be imaged and determining a temperature of an x-ray detector used to acquire the radiographic data. The method also includes comparing the temperature of the x-ray detector to a database of temperature-dependent gain maps and selecting a temperature-dependent gain map from the comparison. The selected temperature-dependent gain map is then applied to the radiographic data acquired to reduce artifacts in a reconstructed image of the subject.

The present invention is also directed to a method of x-ray data correction. The method includes the steps of acquiring radiographic data from a subject to be imaged and determining a temperature of an x-ray detector used to acquire the radiographic data. The method further includes the steps of comparing the temperature of the x-ray detector to a temperature-dependent x-ray detector sensitivity curve and identifying a conversion factor from the comparison, as well as applying the identified temperature-dependent conversion factor to the radiographic data acquired to achieve a desired brightness in a reconstructed image of the subject.

A method of calibrating an offset image for x-ray data correction is disclosed. The method includes determining a time interval between acquisition of radiographic image data and acquisition of offset image data and determining a magnitude of a power mode transient between the acquisition of radiographic image data and the acquisition of offset image data from the time interval. The method also includes selecting an offset data correction map from a number of offset data correction maps. The selected offset data correction map is designed to reduce a difference between artifacts in the offset image data and the radiographic image data attributable to the power transient.

The present invention has been described in terms of the preferred embodiment, and it is recognized that equivalents, alternatives, and modifications, aside from those expressly stated, are possible and within the scope of the appending claims.

What is claimed is:

1. An x-ray imaging system comprising:
   an x-ray detector configured to detect radiation attenuation through a subject to be imaged and output imaging data in response thereto;
   at least one thermal sensor configured to sense a temperature of the x-ray detector and provide temperature feedback of the x-ray detector;
   a processor operationally connected to receive the temperature feedback from the at least one thermal sensor and apply a correction to the output of the x-ray detector specific to the temperature of the x-ray detector;
   wherein the processor is further configured to automatically select a calibration map from a plurality of calibration maps for calibrating the x-ray detector based on the temperature of the x-ray detector during data acquisition; and
   wherein the processor is further configured to measure a time interval between acquisition of image data and acquisition of a subsequent offset data acquisition, and augment the offset data acquisition according to an offset data correction map to reduce artifacts due to power mode transients.

2. The x-ray imaging system of claim 1 wherein each of the plurality of calibration maps comprises calibration data corresponding to one temperature.

3. The x-ray imaging system of claim 1 wherein the processor is further configured to select the calibration map by interpolating between two calibration maps.

4. The x-ray imaging system of claim 1 wherein the processor is further configured to apply the selected calibration map to reduce temperature-sensitive artifacts in a reconstructed image of the subject.

5. The x-ray imaging system of claim 4 wherein the x-ray detector includes a scintillator configured to emit light in response to reception of radiation and a detector element array having a plurality of detector elements, each detector element configured to detect light from the scintillator and provide an electrical signal that may be processed for image reconstruction, and each detector element having a temperature-variant response.

6. The x-ray imaging system of claim 1 wherein the plurality of calibration maps also includes gain correction maps and bad pixel maps, and wherein the processor is further configured to automatically select a gain correction map and a bad pixel map for calibrating the x-ray detector based on the temperature of the x-ray detector during data acquisition.

7. The x-ray imaging system of claim 1 wherein the processor is further configured to receive temperature feedback during the time interval following the imaging data acquisition and apply a temperature-dependent offset correction to the imaging data based on the temperature of the x-ray detector at the time interval.

8. The x-ray imaging system of claim 1 wherein the x-ray detector, at least one thermal sensor, and processor are enclosed in a common cover assembly.

9. A method of calibrating an offset image for x-ray data correction comprising the steps of:
   determining a time interval between acquisition of radiographic image data and acquisition of offset image data;
   determining a magnitude of a power mode transient between the acquisition of radiographic image data and the acquisition of offset image data from the time interval;
   selecting an offset data correction map from a number of offset data correction maps, the selected offset data correction map designed to reduce a difference between artifacts in the offset image data and the radiographic image data attributable to the power transient;
   applying the offset data correction map to the acquired offset image data;
   reconstructing an image based upon the radiographic image data and the offset image data; and
   displaying the image to a user.

* * * * *